United States Patent [19]

Foote et al.

[11] Patent Number: 5,135,488
[45] Date of Patent: Aug. 4, 1992

[54] SYSTEM AND METHOD FOR MONITORING, DISPLAYING AND RECORDING BALLOON CATHETER INFLATION DATA

[75] Inventors: Jerrold L. Foote; Darla R. Gill; Fred P. Lampropoulos, all of Salt Lake City, Utah

[73] Assignee: Merit Medical Systems, Inc., Salt Lake City, Utah

[21] Appl. No.: 324,938

[22] Filed: Mar. 17, 1989

[51] Int. Cl.⁵ .................................................. A61M 29/02
[52] U.S. Cl. ........................................ 604/97; 604/96; 604/99; 604/100; 606/192
[58] Field of Search .................................. 604/96–106; 606/192–194; 128/672–675

[56] References Cited

U.S. PATENT DOCUMENTS

| | | |
|---|---|---|
| 383,940 | 6/1888 | Brinkerhoff . |
| 404,105 | 5/1889 | Overlach . |
| 466,125 | 2/1891 | Schirmer . |
| 577,682 | 2/1897 | Eissner . |
| 730,054 | 6/1903 | Sheets . |
| 1,661,818 | 3/1928 | Cook . |
| 1,707,880 | 4/1929 | Sheets . |

(List continued on next page.)

FOREIGN PATENT DOCUMENTS

| | | |
|---|---|---|
| 545415 | 8/1957 | Canada . |
| 1242737 | 8/1960 | France . |

OTHER PUBLICATIONS

"ACS Accessories Offer Optimum Efficiency in our Angioplasty Procedures," Eli Lilly and Company.
"Clearing the Path for a Healthy Heart," *Tristate: The Cincinnati Enquirer Magazine,* Oct. 23, 1988.
"Coronary Angioplasty," Krames Communications, 1985.
"Good News for People with Only Two Hands," SciMed Life Systems, Inc.
"Health-Critics of Angioplasty Worry About Inflated Success Claims," *U.S. News & World Report,* Jul. 25, 1988, p. 65.
"Inflation PRO: A New Dual-Support System for Angioplasty," Baxter Healthcare Corporation.
"PTCA Safe and Efficacious Performed Together With Diagnostic Angiography in Selected Cases," *Cardiovascular News,* May 1988, p. 8.
"USCI Wizard Disposable Inflation Device," C. R. Bard, Inc.

*Primary Examiner*—Robert A. Hafer
*Assistant Examiner*—Kerry Owens
*Attorney, Agent, or Firm*—Workman, Nydegger & Jensen

[57] ABSTRACT

An electronically controlled syringe system for connection to a balloon catheter or other balloon-type member and for automatically monitoring, displaying and recording inflation data when the syringe system is used to inflate the balloon catheter or other balloon-type member. A syringe having a barrel and a syringe plunger is selectively operable to increase fluid pressure applied to the balloon catheter or other balloon member by sliding the plunger further into the barrel. Positive pressure applied to the balloon catheter or member can be released by withdrawing the syringe plunger toward the rear of the barrel. A piezoresistive semiconductor transducer housed on the barrel of the syringe senses positive fluid pressure applied by the syringe. The electric signal output by the transducer is input to a controller where the signal is digitally processed so as to derive and record therefrom electronic data representing the magnitude or applied fluid pressure, and so as also to derive the length of time that positive fluid pressure is applied and the electronic data representing this information is automatically displayed and recorded. The controller is also programmable to permit optional selection and input of various control parameters, such as a maximum positive inflation pressure that is to be applied, maximum duration for applying positive inflation pressure, initialization of the date and time of an inflation procedure and/or retrieving and displaying inflation data previously recorded for any prior inflation of the balloon catheter or other balloon member.

26 Claims, 10 Drawing Sheets

U.S. PATENT DOCUMENTS

| | | | |
|---|---|---|---|
| 2,656,836 | 10/1953 | Hickey | 128/218 |
| 2,672,866 | 3/1954 | Kater | 128/218 |
| 2,699,168 | 1/1955 | Lewis | 128/218 |
| 2,736,315 | 2/1956 | Feeney | 128/218 |
| 3,080,866 | 3/1963 | Friedman | 128/218 |
| 3,388,941 | 6/1968 | Marcus | 294/1 |
| 3,478,937 | 11/1969 | Solowey | 222/386 |
| 3,491,757 | 1/1970 | Arce | 128/221 |
| 4,057,050 | 11/1977 | Sarstedt | 127/2 |
| 4,063,662 | 12/1977 | Drummond | 222/31 |
| 4,254,773 | 3/1981 | Waldbillig | 128/348 |
| 4,267,846 | 5/1981 | Kontos | 128/765 |
| 4,444,335 | 4/1984 | Wood | 222/43 |
| 4,466,426 | 8/1984 | Blackman | 128/1.1 |
| 4,651,738 | 3/1987 | Demer et al. | 604/96 |
| 4,710,179 | 12/1987 | Haber et al. | 604/211 |
| 4,715,854 | 12/1987 | Vaillancourt | 604/191 |
| 4,743,230 | 5/1988 | Nordquest | 604/97 |
| 4,758,223 | 7/1988 | Rydell | 604/98 |
| 4,781,192 | 11/1988 | Demer | 604/97 X |
| 4,858,615 | 8/1989 | Meinema | 128/668 |
| 4,872,483 | 10/1989 | Shah | 604/99 X |
| 4,877,035 | 10/1989 | Bogen et al. | 128/673 |
| 4,896,671 | 1/1990 | Cunnigham et al. | 606/39 X |
| 4,901,731 | 2/1990 | Millar | 128/675 | ns
SYSTEM AND METHOD FOR MONITORING, DISPLAYING AND RECORDING BALLOON CATHETER INFLATION DATA

Appendix A, referred to herein, may be found in the microfiche appendix contained in the PTO file for this patent document. The microfiche appendix is comprised of one microfiche having twenty seven frames.

A portion of the disclosure of this patent document contains material to which a claim of copyright protection is made. The copyright owner has no objection to the reproduction by anyone of the patent document or the patent disclosure as it appears in the Patent and Trademark Office patent file or records, but reserves all other rights with respect to the copyrighted work.

BACKGROUND OF THE INVENTION

1. Field of the Invention

This invention relates to syringe systems that are used for controlling the inflation of a balloon-tipped catheter, and more particularly to a system and method which utilize an electronically monitored syringe system to assist in the control of balloon catheter inflation pressures and to automatically record balloon catheter inflation data.

2. The Present State of the Art

Balloon-tipped catheter systems have been known and used in the medical arts for a number of years in connection with a variety of different kinds of procedures which are used, for example, in various fields of medicine, such as urology, gynecology, cardiology and others. Particularly in connection with the treatment of coronary artery disease, the use of balloon-tipped catheters and their associated syringe systems have become widely used.

Coronary artery disease is the narrowing of the arteries that feed oxygen-rich blood to the heart. Since the heart is a muscle whose primary job is to pump oxygenated blood throughout the body, the heart needs adequate amounts of oxygen to properly function. Thus, when the coronary arteries which are located on the top of the heart and through which oxygenated blood is returned to the heart become narrowed or blocked (a condition known as "stenosis"), angina can result. Angina is a symptom of coronary artery disease characterized by chest pain or pressure that can radiate to the arm or jaw, and is caused by a lack of oxygen-rich blood to the heart muscle. Coronary artery disease with its accompanying symptom of angina results from atherosclerosis, which is a build up of waxy material called plaque inside the arteries. When this happens, under exertion or stress, the heart demands more oxygen but the narrowed coronary arteries cannot supply enough oxygen-rich blood to meet the demand, resulting in angina.

Up until about ten years ago, there were two basic ways to treat coronary artery blockages: with medicine or by performing coronary artery by-pass surgery. Various kinds of medication could be administered which would decrease the work of the heart by slowing the heart rate, dilating the blood vessels, or lowering blood pressure. However, such medicinal treatment did not cure coronary artery blockage, which thus remained and which would therefore continue to present a risk that at some point the blockage would become serious enough to require surgical intervention.

In coronary artery by-pass surgery, a blood vessel from the chest or leg is grafted beyond the point of blockage so that the blood detours past the blockage in order to reach the heart In some severe cases, multiple by-passes are performed. As is well known, coronary artery by-pass surgery is expensive, is a high risk procedure and often requires prolonged hospitalization and recovery periods.

About ten years ago, another method for treating coronary artery disease was developed, called balloon coronary angioplasty, or more technically, percutaneous transluminal coronary angioplasty (PTCA). PTCA is a much less traumatic procedure than coronary artery by-pass surgery. PTCA takes about two hours and can be done under local anesthesia, with the result that often a patient can be back on his feet and active in a matter of days. Because PTCA is much less expensive and less traumatic than by-pass surgery and yet in many cases still effectively removes blockage, PTCA has experienced a dramatic increase in the number of such procedures performed each year. For example, according to some reports, as recently as 1987 some 200,000 patients suffering from coronary artery disease were treated by PTCA. Since coronary artery disease remains the number one cause of death, with (as of 1987) some six million reported cases in the U.S. alone, PTCA may be expected to continue to play an important role in the treatment of coronary artery disease.

In performing PTCA, an introducer sheath is inserted through an incision made in the groin or in the artery of an arm. An x-ray sensitive dye is injected into the coronary artery through a catheter that is introduced through the sheath The dye enables the doctor, through the use of real time x-ray techniques, to clearly view the arteries on a television monitor and to thereby locate the artery blockage. A balloon-tipped catheter with a guide wire at the end of it is then advanced through the artery to the point of the blockage with the help of the x-ray monitor.

As schematically illustrated in FIGS. 1A-1C, the balloon catheter 10 is advanced to the middle of the blockage 12. The catheter 10, which is filled with a fluid and is coupled at its other end to a control syringe, is manipulated by the cardiologist. Once the balloon catheter is in place, utilizing the control syringe the balloon is inflated for 20 to 60 seconds as shown in FIG. 2B. The balloon is then deflated and this procedure is repeated typically several times to compress the plaque on the arterial wall, as shown in FIG. 1C. After the results are checked, the balloon catheter and guide wire are then removed.

As will be appreciated, notwithstanding that PTCA is a much less traumatic procedure than coronary artery by-pass surgery, nonetheless exacting control with respect to inflation pressure and duration of the inflation periods is essential to the safety of the patient. For example, when the balloon catheter is completely inflated so as to begin compressing the plaque, blood flow to the heart is thereby temporarily shut off. This creates the potential for initiating cardiac arrest. Accordingly, the pressure exerted on the artery by the balloon catheter as well as the duration of the blockage created by inflating the balloon catheter must both be carefully controlled by the attending cardiologist and other personnel. The inflation pressures and duration of each inflation must be based on the cardiologist's assessment of the health of the patient and the patient's ability to withstand such a temporary stoppage of blood flow to the heart.

In the past, PTCA syringe systems have utilized syringe systems which are equipped with standard pressure gauges that are utilized to sense and read the pressure used for purposes of inflating a balloon catheter. Human observation of stop clocks and the like has been used to control the duration of the inflation.

While these prior art techniques have been widely used with success, there is still a serious risk of human error when using such systems. The gauges used on such syringe systems are often awkward and difficult to accurately read, and are also subject to malfunction. Thus, improper recording of inflation pressure and/or duration may occur. Accordingly, there is a need for the cardiologist and/or clinician to be able to improve the degree of control and precision with respect to the inflation procedure. There is also a need to be able to accurately record the procedure data so that in the event of any later question with respect to whether the procedure was properly carried out, there is an accurate record from which to answer such questions. The system and method of the present invention provide an effective solution to these problems which have not heretofore been fully appreciated or solved.

SUMMARY OF THE INVENTION

The system and method of the present invention have been developed in response to the present state of the art, and in particular, in response to the problems and needs in the art not heretofore fully or completely solved by syringe inflation systems used in connection with PTCA procedures. However, it is not intended that the system and method of the present invention will necessarily be limited solely to PTCA procedures, since they will also find useful application with potentially many kinds of procedures which require the utilization of inflatable balloon members for various kinds of medical procedures. Thus, it is an overall object of the present invention to provide a system and method which provide for more accurate measurement, monitoring and recording of the pressures used for inflation of a balloon-type member as well as the duration of inflation in connection with any such inflation of a balloon-type member, catheter or otherwise.

Another important object of the present invention is to provide a system and method whereby state of the art electronic technology can be utilized to assist the cardiologist or clinician in accurately measuring, monitoring and recording inflation pressures which he or she desires to achieve when utilizing a syringe system to inflate a balloon catheter or other balloon-type member, and which will at the same time automatically electronically record and store the inflation pressure and duration of the inflation so as to permit the data pertaining to the procedure to be later printed out and thus accurately documented and saved for later reference.

Another important object of the present invention is to provide an improved syringe system and electronic monitoring and recording system which increase the convenience and safe utilization of a balloon catheter or other balloon-type inflation member.

These and other objects and features of the present invention will become more fully apparent from the following more detailed description taken in conjunction with the drawings and claims, or may be learned by the practice of the invention.

Briefly summarized, the foregoing and other objects are achieved in an electronically monitored syringe system that is connected to a balloon catheter or other inflatable balloon-type device through tubing. The syringe comprises a barrel and a plunger selectively operable to increase fluid pressure applied to the balloon catheter through the connecting tubing by sliding the plunger further into the barrel, and to then remove the applied pressure by returning the plunger to the rear of the barrel. A transducer means for sensing fluid pressure applied by the syringe is placed in fluid communication with the syringe and the connecting tubing. The transducer means thereby senses applied fluid pressure and outputs an electrical signal proportional to the sensed pressure. The electrical signal output by the transducer means is then electronically processed so as to derive and record therefrom electronic data representing the magnitude of fluid pressure applied to the balloon catheter or other balloon-type member, and so as also to derive the length of time that inflation pressure is applied to the balloon catheter or other balloon-type member, and the electronic data representing these parameters is then automatically displayed and/or recorded. The system also comprises a display means for selectively outputting a visual display of the magnitude of the applied pressure and the corresponding length of time that inflation pressure is applied to the balloon catheter or other balloon-type member with respect to each inflation thereof.

The electronic control system used in conjunction with the system and method of the present invention may also be optionally designed to permit the selection and input of various control parameters such as a maximum positive inflation pressure that is to be applied, a maximum duration for applying positive inflation pressure, initializing the date and time of the procedure and/or retrieving and displaying inflation data previously recorded for any prior inflation of the balloon catheter or other balloon-type member. In this manner, the system and method of the present invention provide not only more convenient operation of the syringe when inflating the balloon catheter or other balloon-type member, but also a much safer and more accurate procedure which can be used to effectively alert a cardiologist or clinician when the appropriate levels of pressure and duration thereof have been reached with respect to a particular inflation event. The system is thus efficient and easy to operate while at the same time providing improved convenience and overall safety, and also providing accurate documentation of all inflation data for later reference.

BRIEF DESCRIPTION OF THE DRAWINGS

The presently preferred embodiments and the presently understood best mode of the invention will be described with additional detail through use of the accompanying drawings, wherein corresponding parts are designated by the same reference numerals throughout, and in which.

DETAILED DESCRIPTION OF THE PRESENTLY PREFERRED EMBODIMENT

The following detailed description is divided into two parts. In part one the overall system is described, including a description of the syringe system, the transducer means and electronic controller by reference to FIGS. 1 through 5. In part two the method by which the system of the present invention is used to electronically monitor, display and automatically record inflation data is described, including a detailed description of one presently preferred method for programming the digital processor used in the electronic controller by reference to FIGS. 6A–6D.

I. THE SYSTEM

A. General Environment and Intended Utility of the System

Figure 1A:
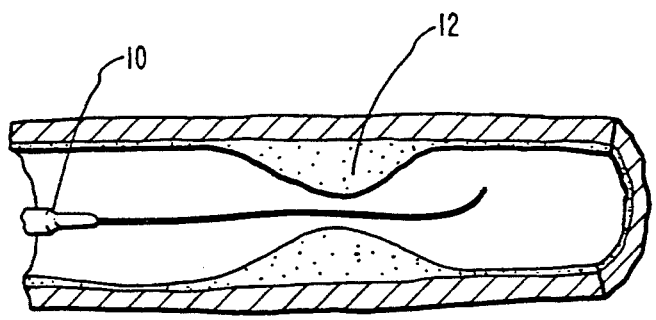
FIGS. 1A-1C are partial cross-sectional views which schematically illustrate a conventional balloon catheter being placed within a vessel such as a coronary artery containing a blockage, and showing the manner in which the blockage is essentially removed by inflation of the balloon catheter.
Figure 1B:
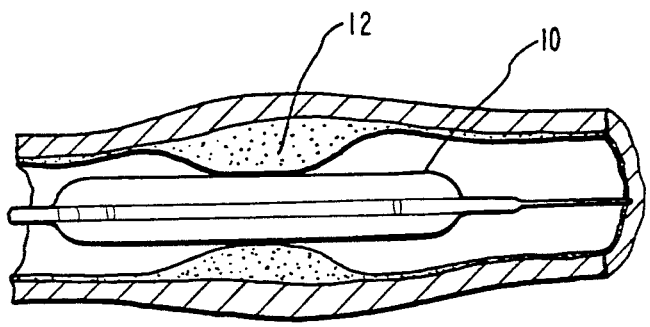
Figure 1C:
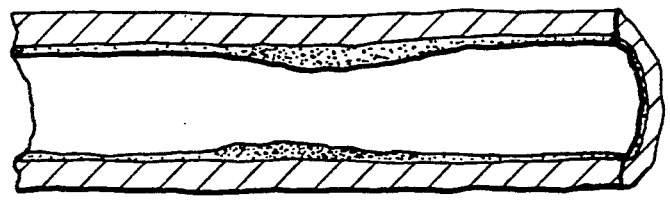

As noted above, the system and method of the present invention have been developed in response to specific needs which have been found to exist in connection with techniques that are currently in use according to the present state of the art which has developed in connection with PTCA procedures. As described in connection with FIGS. 1A–1C, PTCA is a surgical procedure used for treating coronary artery disease wherein a balloon catheter 10 is inserted through an incision made in the groin or in the artery of an arm and is then advanced through the artery by means of a guide catheter and assisted by means of an x-ray sensitive dye. The balloon catheter 10 is advanced until it is located at the middle of the blockage 12. Once located at the middle of the blockage 12, the balloon catheter 10 is then inflated (see FIG. 1B) to a pressure that is typically between 7 and 10 atmospheres for a duration of between 20 to 60 seconds. The balloon catheter 10 is then deflated and the procedure is repeated a number of times, slightly increasing the inflation pressure each time so as to further compress and thereby reduce the blockage 12 created by the buildup of plaque along the wall of the artery. Once this series of inflations is completed and the artery is cleared, as shown in FIG. 1C, the balloon catheter 10 is removed.

While the system and method of the present invention are particularly useful in connection with the aforementioned PTCA procedure, the system and method of the invention are not intended to be necessarily limited to use in connection with PTCA. Rather, it is contemplated that the system and method of the invention will find useful application with respect to any procedure requiring the use of an inflatable balloon-type member. Moreover, while in PTCA the inflation pressure which is applied to the balloon catheter 10 is applied hydraulically by means of the syringe and connecting tubing which are all filled with a sterile liquid such as a solution of saline and contrast medium, in some potential applications it may be necessary or desirable to apply the inflation pressure pneumatically. Accordingly, as used herein the term "fluid pressure" is intended to apply either to a hydraulically or a pneumatically applied inflation pressure.

B. The Presently Preferred Syringe System and Electronic Controller: FIGS. 2–5

The system of the present invention is comprised of a syringe that is connected to a balloon catheter or other balloon-type member through tubing. The syringe is used to apply fluid pressure to the balloon catheter or other balloon-type member through the tubing so as to inflate the balloon catheter or balloon member when desired, and can also be used to deflate the balloon catheter or balloon member after it has been inflated for a selected duration. The system is also comprised of a transducer means for sensing applied fluid pressure and for outputting an electrical signal proportional to the sensed fluid pressure. The transducer means is thus preferably in fluid communication with the syringe and the tubing connected to the balloon catheter or other balloon-type member. The system also comprises an electronic circuit means connected to the transducer means for receiving the electrical signal that is output by the transducer means and for processing the electrical signal so as to derive and record therefrom electronic data representing inflation pressure applied to the balloon catheter or balloon member as well as the length of time the inflation pressure is applied to the balloon catheter or balloon member each time it is inflated. The system is also comprised of display means which is electrically connected to the electronic circuit means for selectively outputting a visual display of the inflation pressure and the corresponding length of time the inflation pressure is applied to the balloon catheter or balloon member during each inflation.

Figure 2:
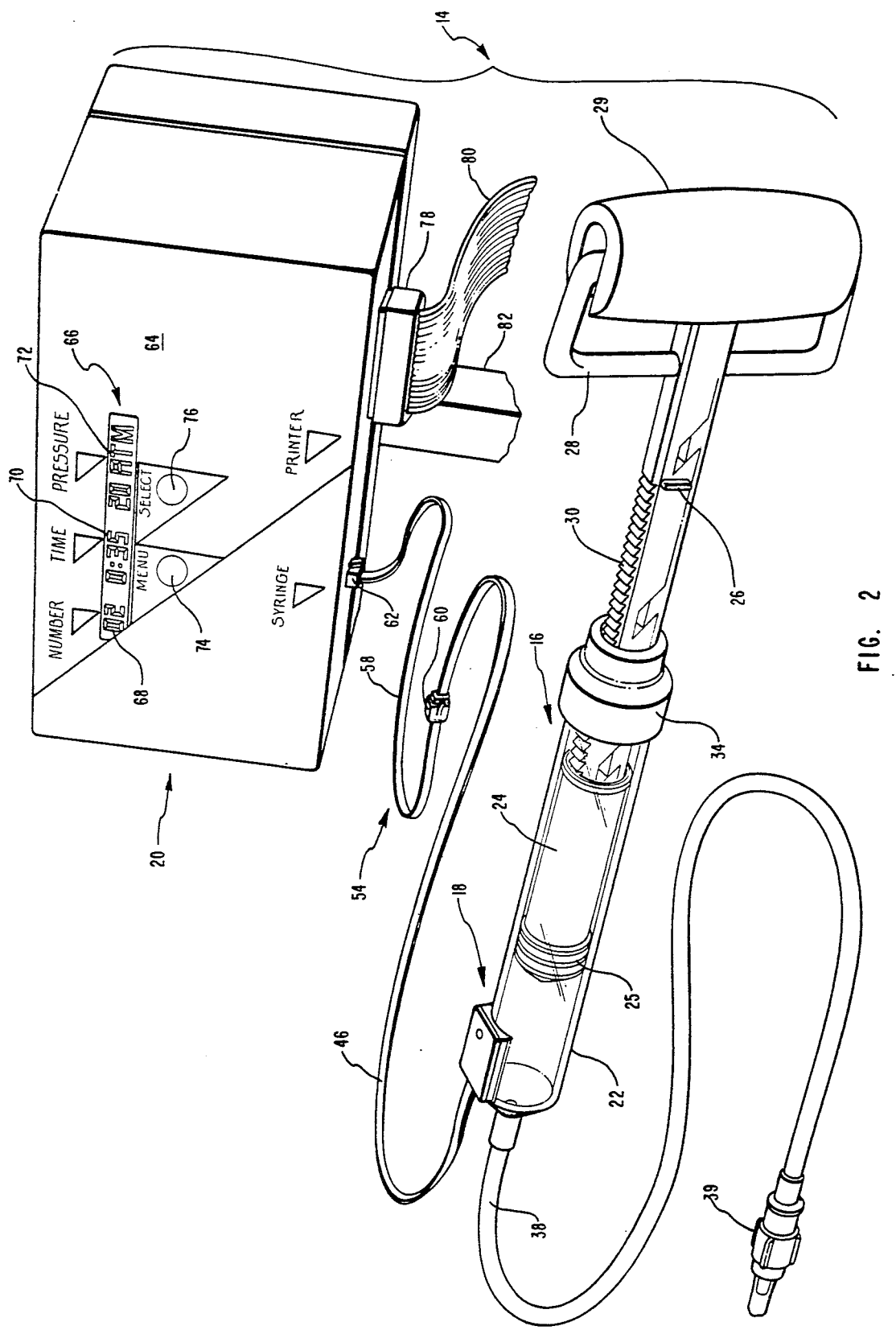
FIG. 2 is a perspective illustration showing the system of the present invention, and in particular illustrating a syringe with tubing for connection to a balloon catheter, and a transducer means mounted on the syringe and electrically connected to an electronic controller.
Figure 3:
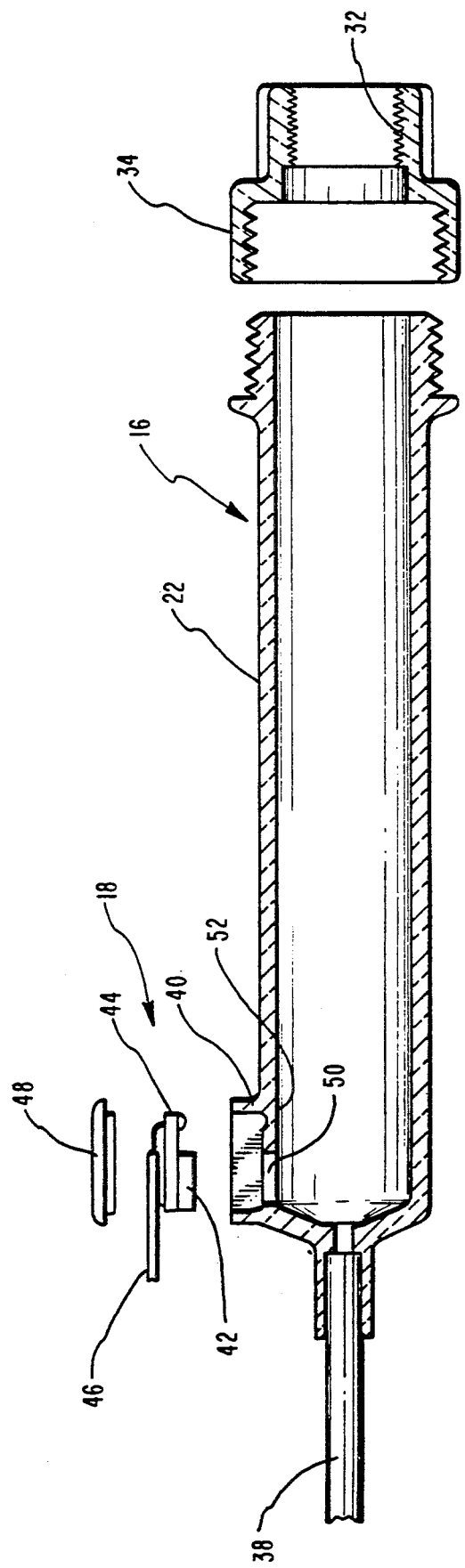
FIG. 3 is a partial cross-sectional view of the syringe barrel that more particularly illustrates one presently preferred structure and method for placing the transducer means in fluid communication with the interior of the syringe and the tubing which is connected to the balloon catheter.

In the preferred embodiment illustrated in FIG. 2, the overall system is generally designated at 14 and the syringe is generally designated at 16. With reference to FIGS. 2 and 3 taken together, the syringe 16 is comprised of a barrel 22 typically molded from transparent plastic material to permit inspection of the contents thereof. A syringe plunger 24 (FIG. 2) is slidably mounted within the barrel and is secured within the barrel 22 of means of a cap 34 which can be threadingly or otherwise securely attached at the end of the barrel 22. The syringe plunger 24 has a threaded portion 30 which mates with corresponding threads 32 (see FIG. 3) of end cap 34.

The proximal end of plunger 24 is provided with a soft rubber bulb 25 which engages the interior of barrel 22 in a fluid-tight fit such that by sliding the syringe plunger 24 further into the barrel 22, positive pressure exerted on the fluid contained within syringe 16 and connecting tubing 38 will be applied to the balloon catheter which is connected to the tubing 38 by means of a rotatable luer connector 39. Similarly, by withdrawing the syringe plunger 24 toward the rear of the barrel 22, the positive pressure exerted on the balloon catheter will be released.

Rapid movement of the syringe plunger 24 is accommodated by means of a trigger mechanism comprising a spring-activated trigger 28 which can be retracted into handle 29 so as to disengage the threads 30 from the corresponding threads 32 of cap 34. This permits the plunger 24 to freely slide in either direction within the syringe barrel 22. By releasing the compression on trigger 28 relative to handle 29, the threads 30 are then permitted to engage the corresponding threads 32 of cap 34 so that thereafter the syringe plunger 24 can only be advanced or retracted by screwing the plunger 24 either clockwise or counter clockwise, respectively. Thus, rapid application or release of pressure applied to the balloon catheter can be accomplished by compressing the trigger 28 against handle 29 followed by movement of the syringe plunger 24 to the position desired for the approximate pressure to be applied. This can then be followed by release of the trigger 28 and screwing the plunger 24, which will permit a slow, gradual adjustment of the syringe plunger 24 to the exact pressure that is desired.

It will be appreciated that insofar as providing for application and release of positive inflation pressure, this function of syringe 16 of the system could be provided by any of a number of syringe systems which are conventional or known in the art. However, the syringe illustrated and generally described in connection with FIGS. 2 and 3 is presently preferred in connection with the system and illustrates the presently contemplated best mode of the syringe 16. A more complete description of syringe 16 and its unique design and advantages is contained in copending U.S. application Ser. No. 325,561, U.S. Pat. No. 5,057,078 filed concurrently herewith, which is incorporated herein by reference.

The transducer means of the system of the present invention is generally designated in FIGS. 2 and 3 at reference numeral 18. As shown best in FIG. 3, the body of syringe barrel 22 has a small rectangular housing 40 formed at the leading end of the barrel as an integral part of the syringe barrel 22. The housing 40 communicates through a small circular opening 50 formed in the sidewall of syringe barrel 22 with the interior of syringe barrel 22 for the purpose of providing fluid communication from the interior of barrel 22 and connecting tubing 38 to the transducer means, as hereinafter more fully described.

As used herein, the term "fluid communication" is intended to mean the pneumatic or hydraulic transmission (direct or indirect) of fluid pressures exerted within the syringe barrel 22 and connecting tubing 38 to the transducer means so that such fluid pressures can be sensed by the transducer means. Direct transmission of such fluid pressures would occur, for example, when a diaphragm of a piezoresistive semiconductor transducer is placed into contact (either pneumatically or hydraulically, or a combination of both) with a fluid contained in a closed system, as would be the case in the preferred embodiment illustrated and described herein. Indirect transmission could be said to occur, for example, where the transducer means is coupled to a diaphragm that in turn contacts the fluid contained in a closed system.

Figure 5A:
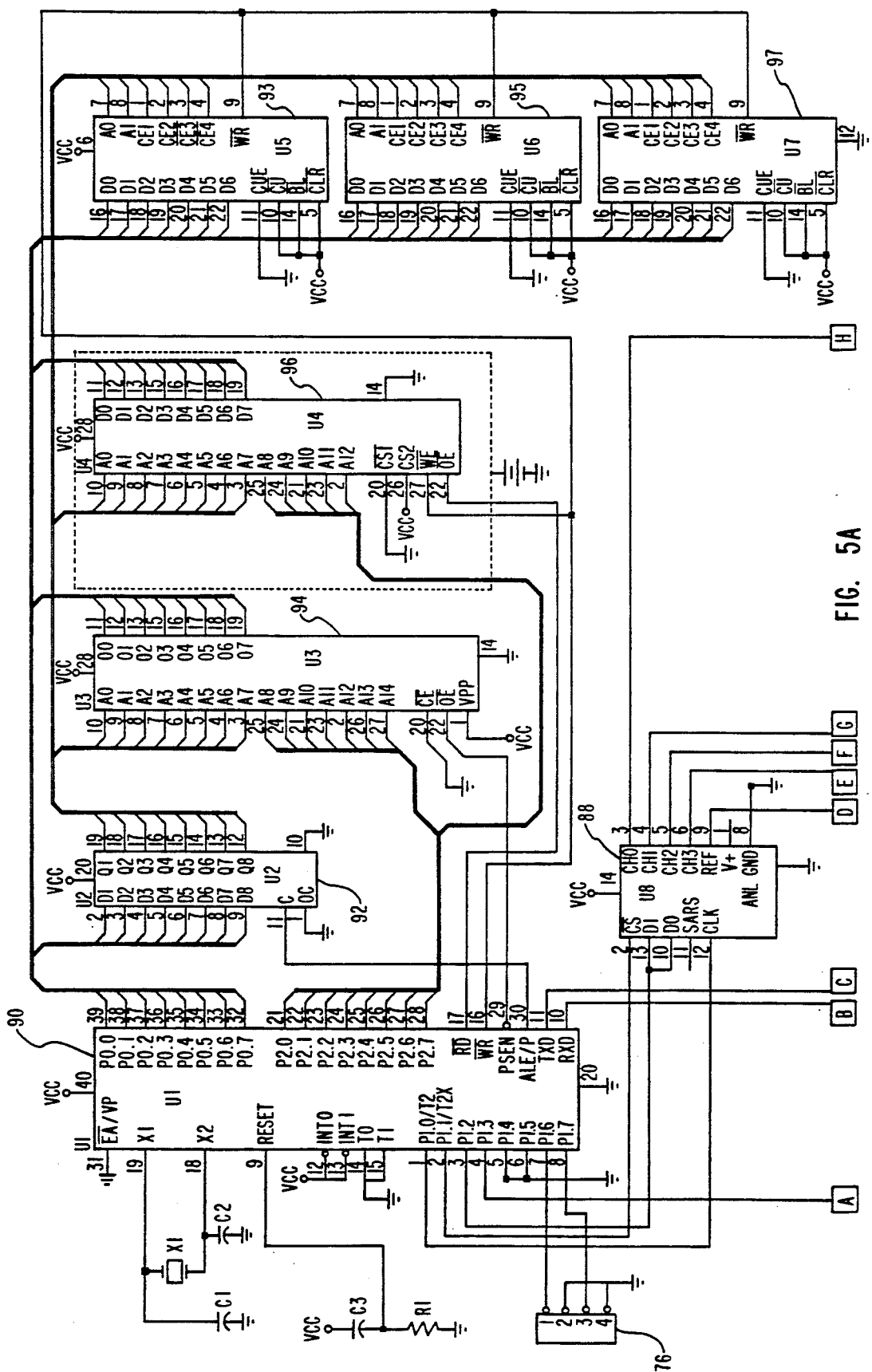
FIGS. 5A and 5B taken together constitute a detailed electrical schematic diagram which illustrate, as an example, the presently preferred embodiment and presently understood best mode for implementing the electronic circuit means of the system and method of the present invention.
Figure 5B:
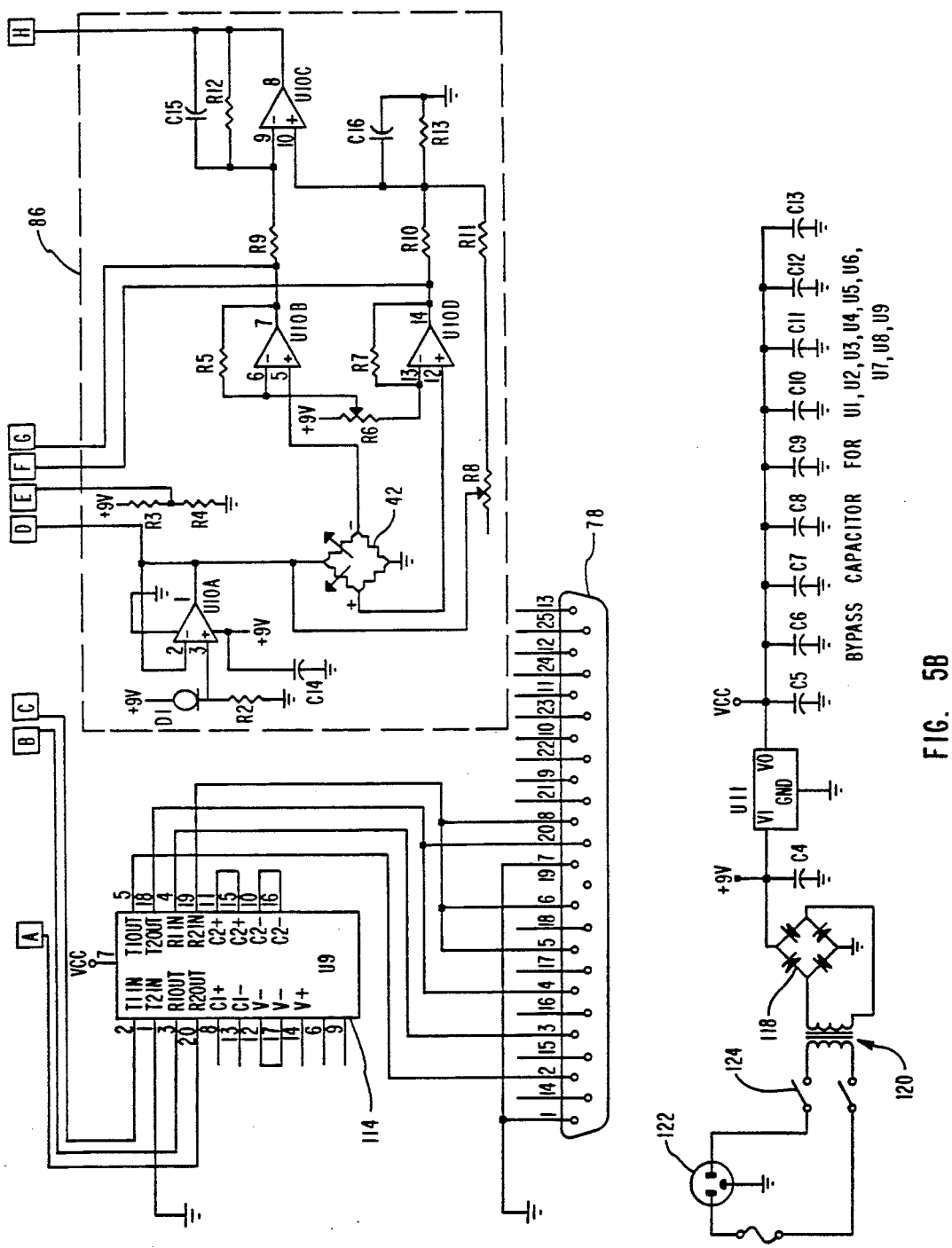

In FIG. 3, the transducer is shown as preferably comprising a piezoresistive semiconductor integrated circuit 42 which provides a Wheatstone bridge, as shown in the detailed electrical schematic at FIG. 5B at the corresponding reference numeral. Transducer 42 is in turn attached to a small ceramic substrate 44 which contains additional circuitry for providing temperature compensation and calibration of the transducer 42, and to which is connected the electrical cable 46. The end of electrical cable 46, ceramic substrate 44 and piezoresistive semiconductor transducer 42 are assembled as illustrated in FIG. 3 and placed within housing 40, and then secured by a suitable potting compound and permanently enclosed by means of the cap 48 placed on top of the housing 40. In this manner, the entire transducer assembly is formed as an integral attachment to the syringe barrel 22. The small circular opening 50 may be filled, for example, with a silicone gel which will permit transmission of the fluid pressures exerted by means of syringe 16 through the circular opening 50 so that such pressures can be sensed by transducer 42, while at the same time isolating the integrated circuit 42 and substrate 44 from coming into contact with fluid contained in the syringe barrel 22.

Stops 26 (see FIG. 1) are formed on the syringe plunger 24 so as to prevent the bulb 25 of syringe plunger 24 from being inserted to the point where it would otherwise close off the circular opening 50.

While in the preferred embodiment the transducer means has been illustrated and described as a piezoresistive semiconductor which is integrally mounted to the syringe barrel 22, it should be appreciated that the preferred embodiment is illustrative only and is not to be construed as limiting the scope of the invention. For example, the semiconductor transducer could be located at the end of connecting tubing attached through a T-connector to tubing 38 and could therefore be located at a position remote from the syringe 16, as for example on an I.V. stand or mounted as part of the electronic circuitry contained inside of controller 20. Furthermore, the transducer means could also comprise transducer types other than the piezoresistive semiconductor type illustrated and described in the preferred embodiment, as for example conventional strain gauge transducers which have been known and used in the art for many kinds of different pressure monitoring applications, or fiberoptic transducers.

With further reference to FIG. 2, the electrical cable generally designated at 54 is comprised of two lengths as shown at 46 and 58. The first length 46 of cable 54 is permanently attached at one end to transducer 18 in the manner described above in connection with FIG. 3. The other end of length 46 terminates in a conventional connector 60 which attaches to the second length 58 of cable 54. The second length 58 of cable 54 in turn attaches by a conventional connector 62 to the electronic circuitry contained in controller 20. Advantageously, by providing a point at connector 60 which is intermediate the transducer 18 and controller 20, transducer 18 and syringe 16 can be disconnected from the controller 20 so that the syringe 16 can be conveniently moved to a different location for testing or the like while still maintaining the sterility of syringe 16 and transducer 18. Thus, while the controller 20 may not necessarily be sterile, sterility of the first length of cable 46 and the transducer 18 and syringe 16 can be maintained at all times.

With continued reference to FIG. 2, the electronic circuit means and display means of the system of the present invention are illustrated in the preferred embodiment as comprising part of controller 20. The specific electronic circuitry which is used for purposes of processing the electrical signals output by transducer 18 through cable 54 is contained inside of controller 20 and is more particularly illustrated in FIGS. 4 and 5A-5B, as hereinafter more fully described. The display means of the system is shown in the illustrated embodiment as comprising, in addition to corresponding parts of the electronic circuitry, a digital readout as generally designated at 66 which is part of the control panel 64.

Specifically, control panel 64 comprises a menu switch 74 which, when activated, will cause a series of optionally selectable functions to be displayed at the digital readout 66. Select switch 76 of control panel 64 can then be used to input various control parameters as well as causing the controller 20 to retrieve and display previously recorded data, as hereinafter more fully described. Controller 20 is also equipped with a conventional connector 78 for a printer cable 80 so that data which is recorded by controller 20 can also be selectively printed out for permanent documentation and later reference.

The digital readout 66 of control panel 64 is shown in the illustrated embodiment as comprising a conventional LED or LCD alphanumeric display having twelve or any other suitable number of controllable display positions for outputting numbers or letters. The display 66 is preferably also divided into a display portion 68 ("NUMBER") which displays and records the number of each discrete inflation of the balloon catheter. A second display portion as illustrated at 70 ("TIME") is used for purposes of checking and/or inputting the current date and time, as well as inputting control data with respect to a maximum duration for applied positive pressure, as desired, and is also used for purposes of displaying the duration of the inflation and signalling a system user if a selected time of duration has been reached. Display portion 72 ("PRESSURE") is similarly used for purposes of inputting selected control data with respect to a maximum positive inflation pressure desired in connection with any inflation, and also selection of the pressure units (e.g., either atmospheres or pounds per square inch), and is also used to display the current inflation pressure and to signal the user if a selected maximum inflation pressure has been reached.

Controller 20 can be conveniently located on a stand 82 at a point which is easily visible by the cardiologist or clinician using the system and can be switched on or off using a conventional switch located on the controller 20. The controller 20 is also plugged into a conventional AC wall outlet from which the power is derived for purposes of running the controller 20, and is also provided with a battery-backed memory which provides an internal clock and timer, and which retains data after the controller 20 is switched off.

Figure 4:
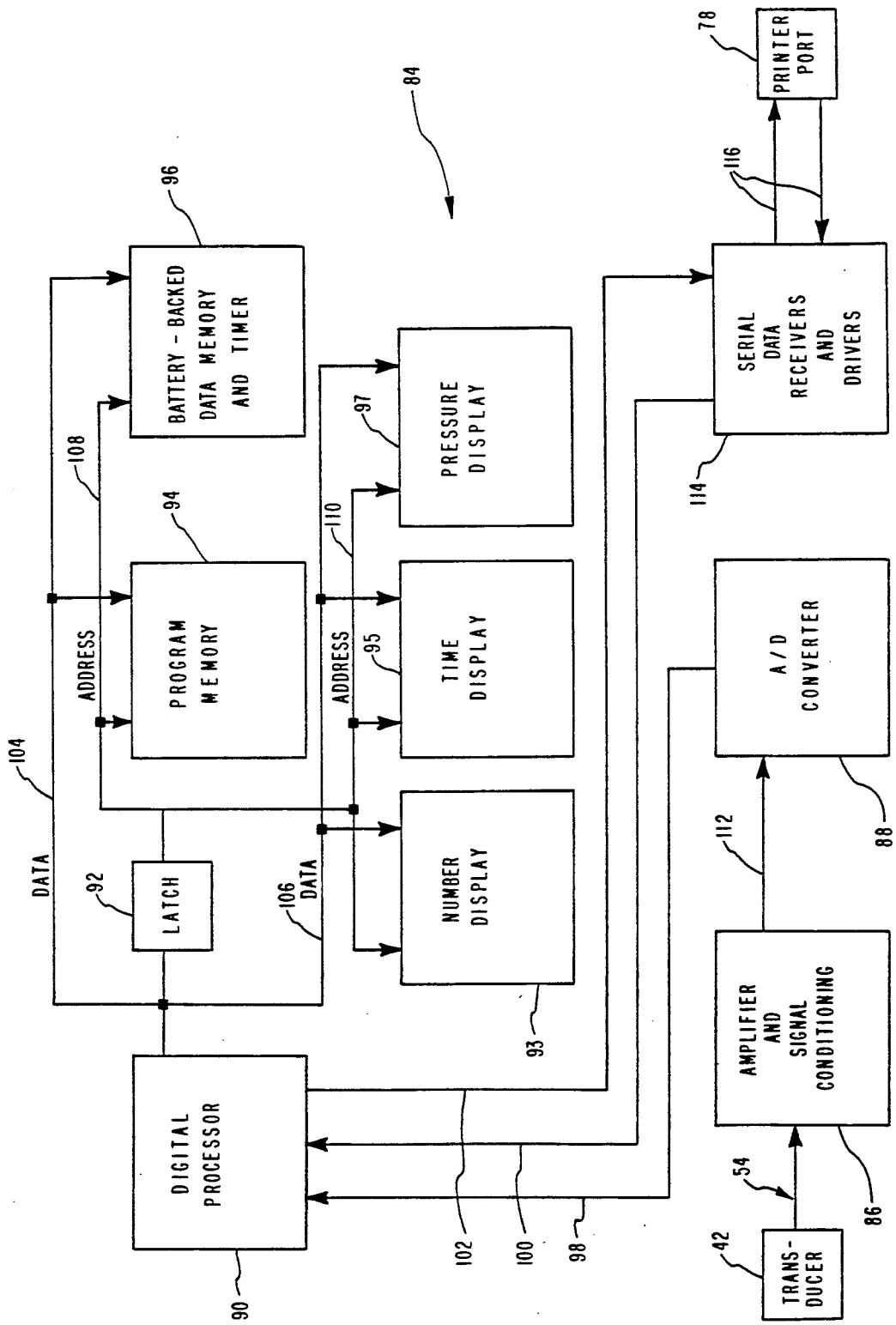
FIG. 4 is a functional block diagram which schematically illustrates the primary components of one presently preferred electronic circuit used in connection with the electronic controller.

With reference next to FIG. 4, the electronic circuit means of the system is more particularly illustrated. In the presently preferred embodiment, the electronic circuit means comprises, by way of example, means for amplifying the electrical signal output by the transducer means; means for converting the amplified signal from an analog to a digital form; digital processor means for processing the digital form of the signal so as to derive therefrom digital data from which the magnitude of the applied pressure, the length of time that pressure is applied to the balloon catheter and whether the applied pressure corresponds to a first or a subsequent inflation of the balloon catheter may be output in a numerical form; data memory means for storing the digital data derived by the digital processor; and program memory means for storing machine-readable instructions utilized by the digital processor means to derive, store, retrieve and display digital data and to optionally display a series of functions for selection at the display means of various control parameters.

With particular reference to the presently preferred embodiment of the electronic circuit means as generally designated at 84 in FIG. 4, the transducer 42 is electrically connected by means of cable 54 to an analog circuit 86 which provides amplification and signal conditioning. As more particularly illustrated in FIG. 5B by the portion of the circuit enclosed by the dashed box 86, the amplifier and signal conditioning circuit 86 is shown in the preferred embodiment as a 100 millivolt full scale differential amplifier with an adjustable differential gain of forty to one, which is provided by amplifiers U10B, U10D, and U10C.

From circuit 86 the amplified signal is then input as schematically represented at line 112 in FIG. 4 and as illustrated at terminal H in FIG. 5B to a conventional analog to digital (A/D) converter circuit 88. The A/D converter 88 serves as a means for converting the amplified signal from an analog to a digital form by outputting a series of corresponding digital signals which identify the analog signal sensed and input by the transducer 42. As shown in reference to FIG. 5A, in the presently preferred embodiment the A/D converter 88 is comprised of an integrated circuit U8. The particular integrated circuit U8 used in the implementation of the electronic circuit means, as well as the identification of each of the parts used in the detailed electrical schematic of FIGS. 5A and 5B, is set forth in Table I at the end of the detailed description. It should be appreciated that the particular circuit components and circuit design which is illustrated in FIGS. 5A and 5B are intended merely as an example of the presently preferred embodiment and the presently understood best mode of implementing the overall functions which are represented by the block diagram of FIG. 4. FIGS. 5A and 5B illustrate in detail the electrical schematic diagram showing the pin numbers and interconnections for each of the integrated circuit components and the other circuit elements used in the implementation of the preferred embodiment. Of course other circuit designs can be devised that would also work satisfactorily using either software driven digital processing circuitry or hardware based circuit design.

With continued reference to FIGS. 4 and 5A-5B, the digitized signal is output by A/D converter 88 as schematically represented by line 98 and as illustrated in greater detail in FIG. 5A to a digital processor means 90. Digital processor means 90 is illustrated in FIG. 5A as integrated circuit U1. The digital processor is controlled by machine-readable instructions stored in program memory 94 which are communicated as schematically illustrated in FIG. 4 by means of a data bus 104 running between digital processor 90 and program memory 94. The particular program instructions carried out by the digital processor U1 are more particularly illustrated and described in reference to the flow chart of FIGS. 6A-6D, as hereinafter more fully described in part two, and are addressed by processor U1 through latch circuit 92 and an address bus schematically represented at line 108 (FIG. 4).

Briefly summarized, the instructions stored in program memory 94 are utilized by digital processor means 90 to derive from the digitized data the fluid pressures applied by the syringe 16 to the balloon catheter and to display the sensed pressures at the digital PRESSURE readout 72 of control panel 64 (see FIG. 2). The applied fluid pressures are also automatically recorded by digital processor means 90 and stored in the data memory 96. The output of the digital data to the display 72 is transmitted by way of bus 106 schematically shown in FIG. 4 and the corresponding electronic circuitry 97 (FIGS. 4 and 5A) which is used to drive the display 72. The processor means 90 can also be programmed to display the positive inflation pressure which is output at the LED display 72 in units of either atmospheres or pounds per square inch as selected by the system user by means of using the menu and select switches 74 and 76, as hereinafter more fully explained.

Processor means 90 can also be utilized according to the programmed instructions contained in memory 94 to monitor and thus assist in the control of the maximum positive inflation pressure to be applied to the balloon catheter by inputting at the PRESSURE readout 72 a maximum positive pressure using the menu and select switches. This control parameter is input from the corresponding display circuitry 97 on bus 106 and bus 104 to the data memory 96. Thereafter, once the maximum positive inflation pressure is reached, the digital processor will cause the PRESSURE display 72 to flash thereby signalling the system user that the maximum positive inflation pressure has been reached. This advantageously assists the system user in more carefully controlling and identifying the procedure used with respect to each inflation event.

In a similar manner, a selected duration for which positive inflation pressure is to be applied to the balloon catheter can also be input at TIME display 70 using the menu and select switches. The corresponding display circuitry 95 thus inputs the selected duration time through data buses 106 and 104 to data memory 96. Accordingly, the programmed instructions contained in memory 94 will thereafter cause the processor means 90 to begin counting the duration once positive inflation pressure begins to be applied. The count will be output by processor 90 at the TIME display readout 70 which will flash once the selected duration has been reached, thereby signalling the system user that positive inflation pressure has been applied for the desired length of time. Again, this significantly enhances the ability of the overall system to carefully assist in controlling the inflation procedures according to the selected parameters.

Data memory 96 is battery-backed so as to retain all data stored therein even when controller 20 is switched off, and so as to provide an internal timer for the date and time data and for clocking any selected maximum duration times input as described above.

Each of the control parameters which are input at the TIME and PRESSURE displays are input and stored as noted above in the data memory 96. In this manner, the appropriate control parameters are utilized by the program stored in memory 94 and are also automatically recorded in the data memory 96 for later reference. In a similar manner, once a positive inflation pressure is applied the processor means 90 will automatically time the duration of the positive pressures and this information will likewise be recorded and stored in the data memory 96 for later reference, along with a numerical identification input from the NUMBER display 68 which identifies whether the particular inflation event is the first time the balloon catheter has been inflated or whether the inflation is a subsequent inflation. In this manner, each time the balloon catheter is inflated it is discretely identified and the maximum inflation pressure and time duration data corresponding to that inflation event are not only displayed but are also automatically recorded and stored in the data memory 96.

A latch circuit 92 is used to control the gating of address data from digital processor 90 to the respective memories 94 and 96 and display circuits 93, 95 and 97 as is conventional in the art. In the detailed schematic of FIG. 5A, the latch circuit 92 is illustrated at integrated circuit U2, while the program memory and data memory circuits 94 and 96 are shown as the integrated circuits U3 and U4, the particular specifications of which are identified in Table I. Integrated circuits for the number, time and pressure display circuits 93, 95 and 97 are also shown in FIG. 5A at integrated circuits U5, U6 and U7 with their corresponding identifications in Table I.

In addition to the digital readout 66 the system of the present invention also provides for output of the recorded data from processor means 90 through serial data lines 100, 102 to a serial data receiver and driver circuit 114, which in turn is connected as schematically illustrated at lines 116 to a printer port 78 to which printer cable 80 is connected. The serial data receivers and drivers are shown as a conventional integrated circuit identified at U9 in FIG. 5B, and which is an RS232 driver and serial transmitter.

The supply voltage used for driving the integrated circuits and other active circuit elements shown in the detailed schematic diagram of FIGS. 5A and 5B is supplied by means of a transformer 120 which is connected at its output to a full wave bridge rectifier 118. The output of rectifier 118 is regulated by integrated circuit U11 which is a voltage regulator. The capacitors C5–C13 serve as noise suppression filters for each of the integrated circuits U1 through U9. With further reference to FIG. 5B, the switch 124 represents the switch on the back of the controller 20 which is used to turn the controller on and off and which connects the controller through a conventional cord and socket plug 122 to an AC outlet.

II. The Method

Attention is next turned to a detailed description of the presently preferred method by which the system of the present invention is used to monitor, display and automatically record inflation data, with particular reference to FIGS. 6A-6D which illustrate one presently preferred embodiment of the instructions which may be utilized to control the processor means 90. As will be appreciated by those of ordinary skill in the art, and as noted above, while the system and method as described in reference to the preferred embodiments herein illustrate the system and method as implemented using state of the art digital processing design and corresponding program instructions for controlling the processor, the system and method could also be implemented and carried out using a hardware design which accomplishes the necessary electronic processing, which is thus intended to be embraced within the scope of various of the claims as set forth hereinafter.

Figure 6A:
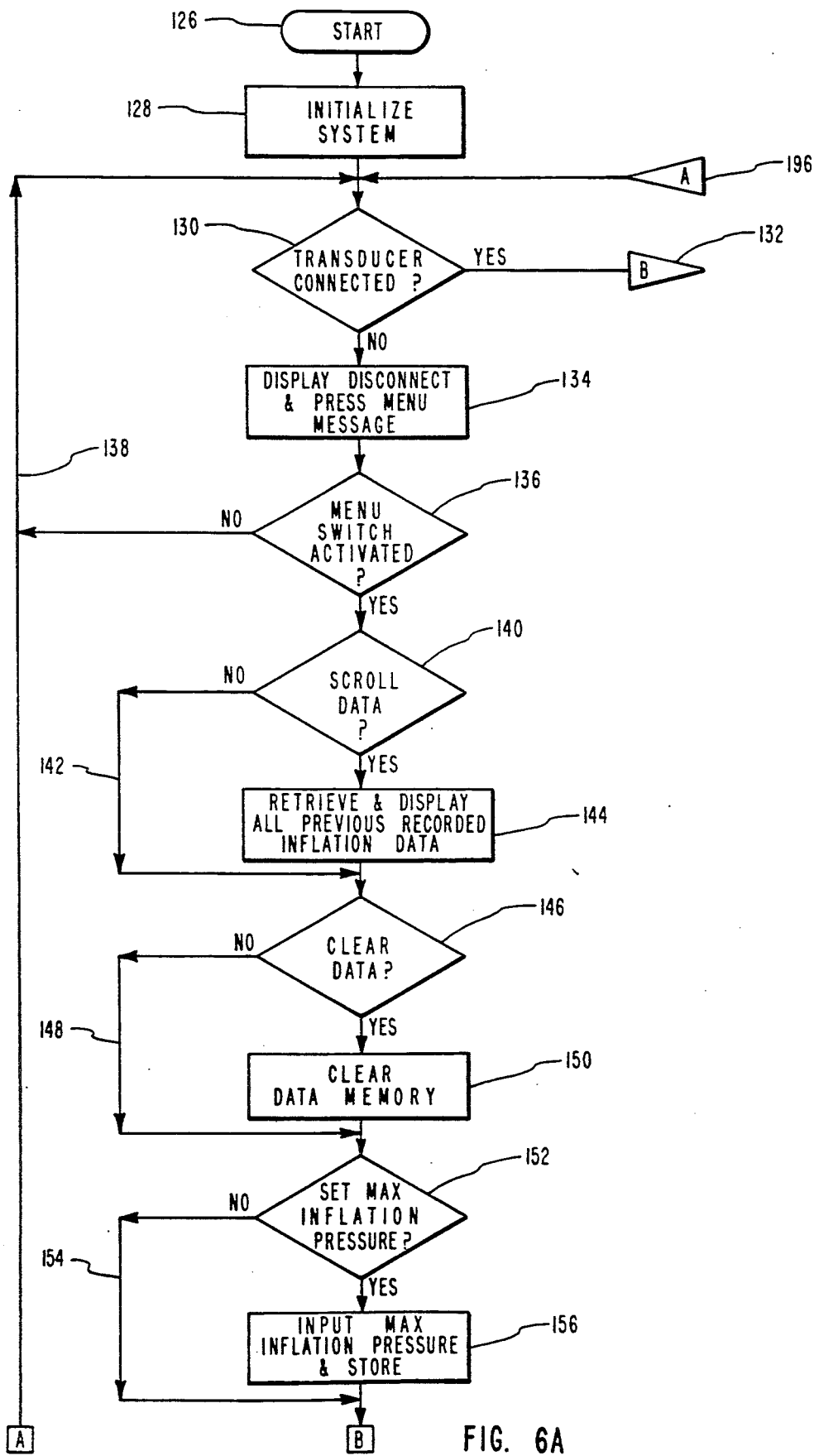
FIGS. 6A through 6D taken together illustrate a flow chart showing one presently preferred method for programming the digital processor of the electronic circuit means in accordance with the method of the present invention.

With reference to FIG. 6A, when the controller 20 is turned on the program starts as indicated at step 126 and then immediately moves to step 128 which causes the system to initialize. At this step, the appropriate program instructions are loaded into the digital processor. The system then moves to step 130 where it checks to determine whether the transducer 42 has been electrically connected by means of the cable 54 to the electronic circuitry housed in controller 20. If the transducer is connected the system then moves as indicated at flag 132 to the portion of the programmed instructions illustrated in FIG. 6C. If the transducer 42 has not yet been electrically connected to controller 20, the system causes a message to be output on the digital readout 66 signifying that the transducer is disconnected (e.g. "NO SYRINGE") and instructing the system user to press the menu switch 74, as shown at step 134. The system then moves to step 136 to check whether the menu switch 74 has been activated and if not returns to step 130 as schematically illustrated at 138 and continues in that loop until the menu switch 74 is activated Once the menu switch 74 is activated at step 136, the system then moves to step 140 and causes the readout 66 to display a message inquiring whether the data previously recorded by the system is to be scrolled (e.g., inflation pressure and duration corresponding to each inflation number is retrieved and displayed in sequence) at the digital readout 66. If the system user desires to review the previously recorded data, the select switch 76 is activated and the system then implements step 144 which causes all of the previously recorded inflation data for each inflation event to be retrieved in sequence and displayed. If at step 140 the system user does not wish to scroll the previously recorded inflation data, the menu switch 74 is again activated which causes the system to skip step 144 as schematically illustrated at line 142 so as to proceed with the next inquiry as represented at step 146.

At step 146 the system causes a message to be displayed on the digital readout 66 inquiring whether previously recorded inflation data which has been stored in the data memory 96 is to be cleared. If select switch 76 is activated this causes the processor to clear the previously recorded inflation data from data memory 96, as indicated at step 150. If the previously recorded inflation data is not to be cleared from data memory 96, the menu switch 74 is activated which causes the system to skip step 150 as illustrated at line 148 and to move to the next inquiry as represented at step 152.

At step 152 the system causes the digital readout 66 to display an inquiry with respect to whether an upper limit is to be set with respect to the maximum positive inflation pressure to be applied with respect to the next inflation event. If so, the select switch 76 is activated and is used to input the selected maximum positive inflation pressure through the data transfer buses 106 and 104 (see FIG. 4), to the data memory 96 for later reference. If a maximum inflation pressure is not selected at step 52, the menu switch is activated which causes the system to skip step 156 and move to the next inquiry as represented at step 158.

At step 158 the system displays a message at the digital readout 66 inquiring whether the maximum duration for application of positive pressure is to be selected. If so, the select switch is again activated which causes the system to move to step 162 and the select switch 76 is then used to input at the time display 70 the selected duration. This selected duration is input by means of the corresponding time display circuitry 95 (see FIG. 4) through the data transfer buses 106 and 104 to the data memory 96 for later reference.

In a manner similar to that described above in connection with the preceding inquiry steps, the system continues to inquire whether the current time and date are to be displayed, as represented at steps 164 and 170, respectively, and if so, by utilizing the select switch 76 as described above, current date and time may be entered at the time display 70. However, the internal clock that is part of the integrated circuit U4 will typically make it unnecessary to enter these parameters. The system then moves through the series of steps represented at 176, 180, 182, and 184 where it determines the pressure units to be displayed at the pressure display 72 as well as determining whether data is to be printed. After the print inquiry has been responded to by utilization of the appropriate menu or select switch 74 or 76 respectively the system returns as illustrated at line 138 to step 130.

As will be appreciated from the foregoing, the portion of the program instructions which are carried out according to the flow chart of FIGS. 6A and 6B pertains to that part of the program which permits a series of optionally selectable functions to be sequentially displayed for purposes of inputting various control parameters which are later utilized in displaying and automatically recording the data, as well as utilizing these control parameters to alert the system user when selected limits are reached with respect to maximum positive inflation pressure and duration of positive inflation pressures.

Figure 6B:
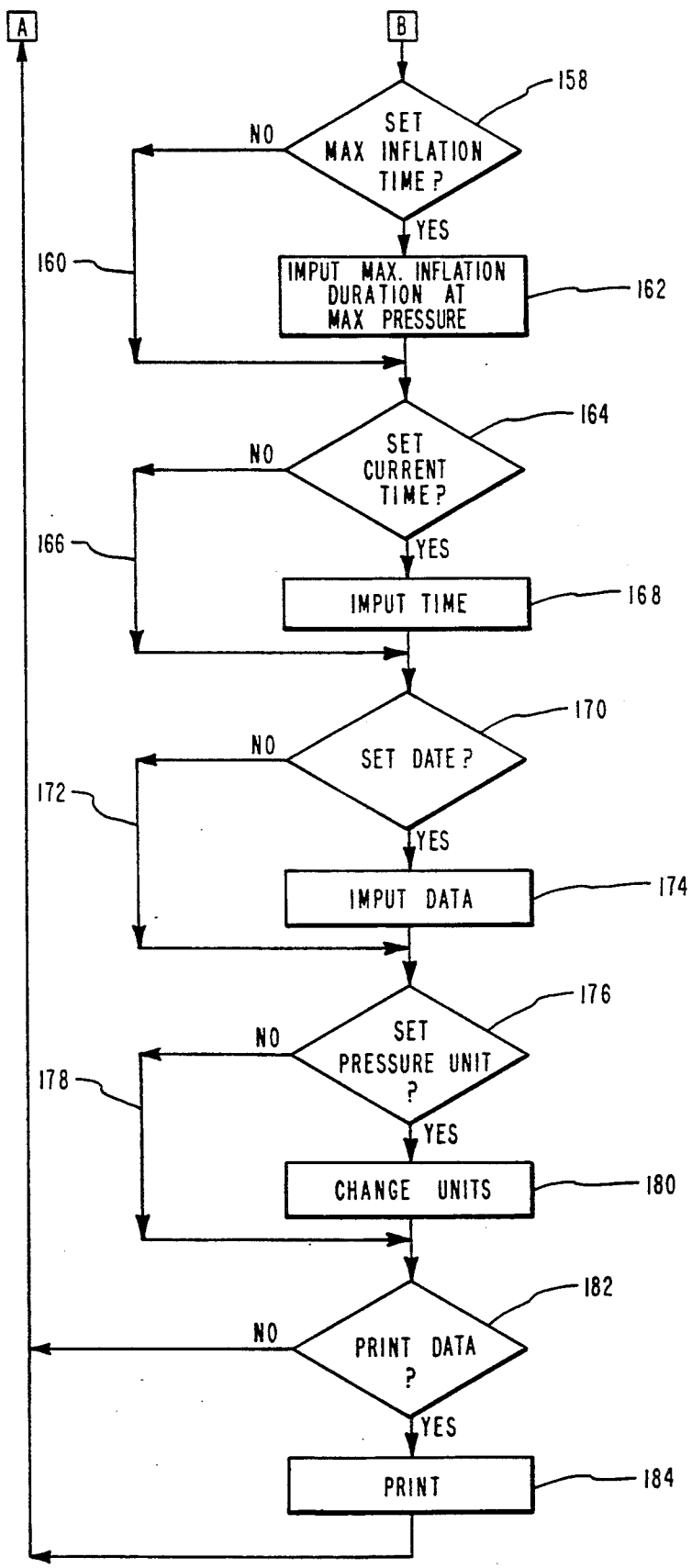
Figure 6C:
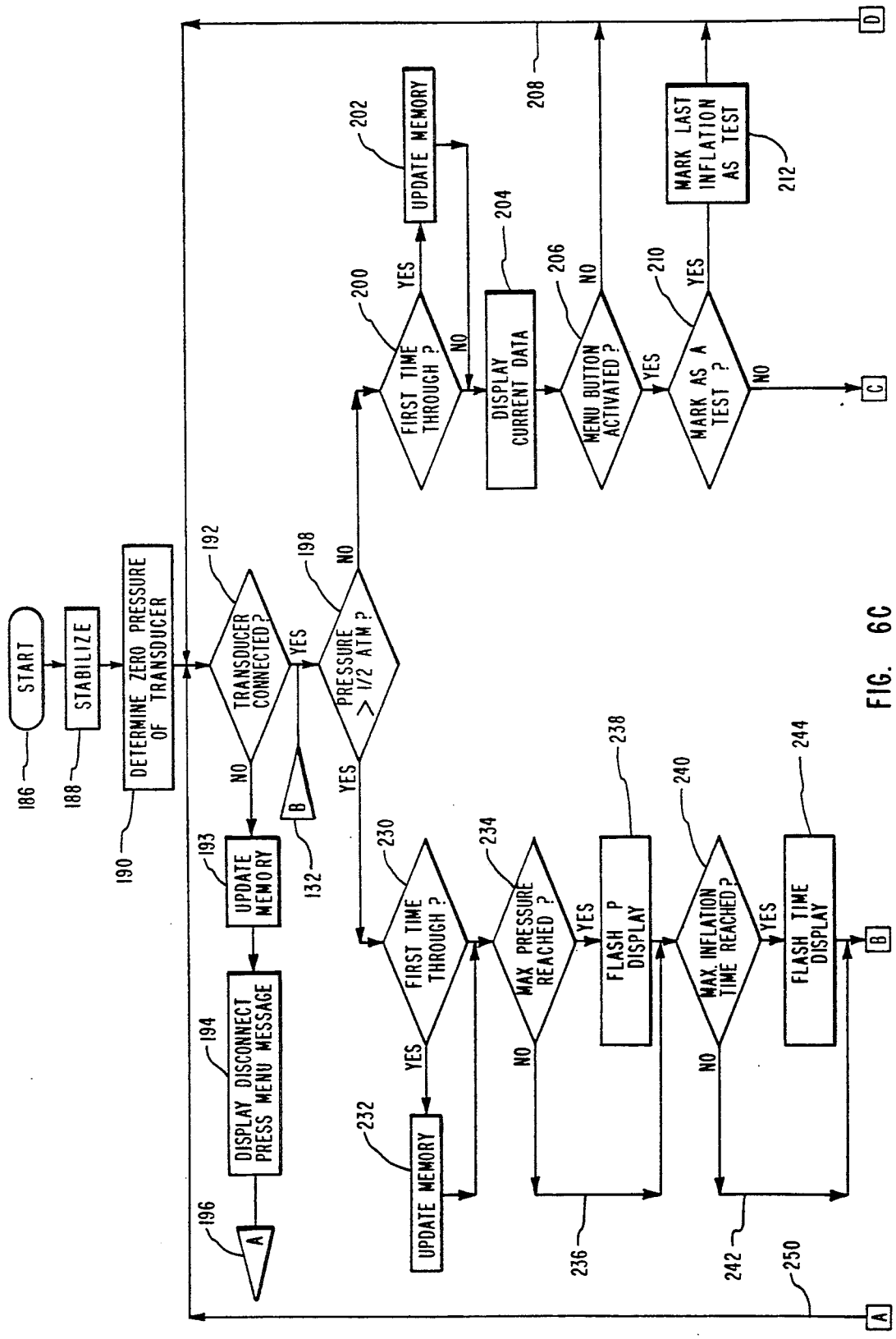
Figure 6D:
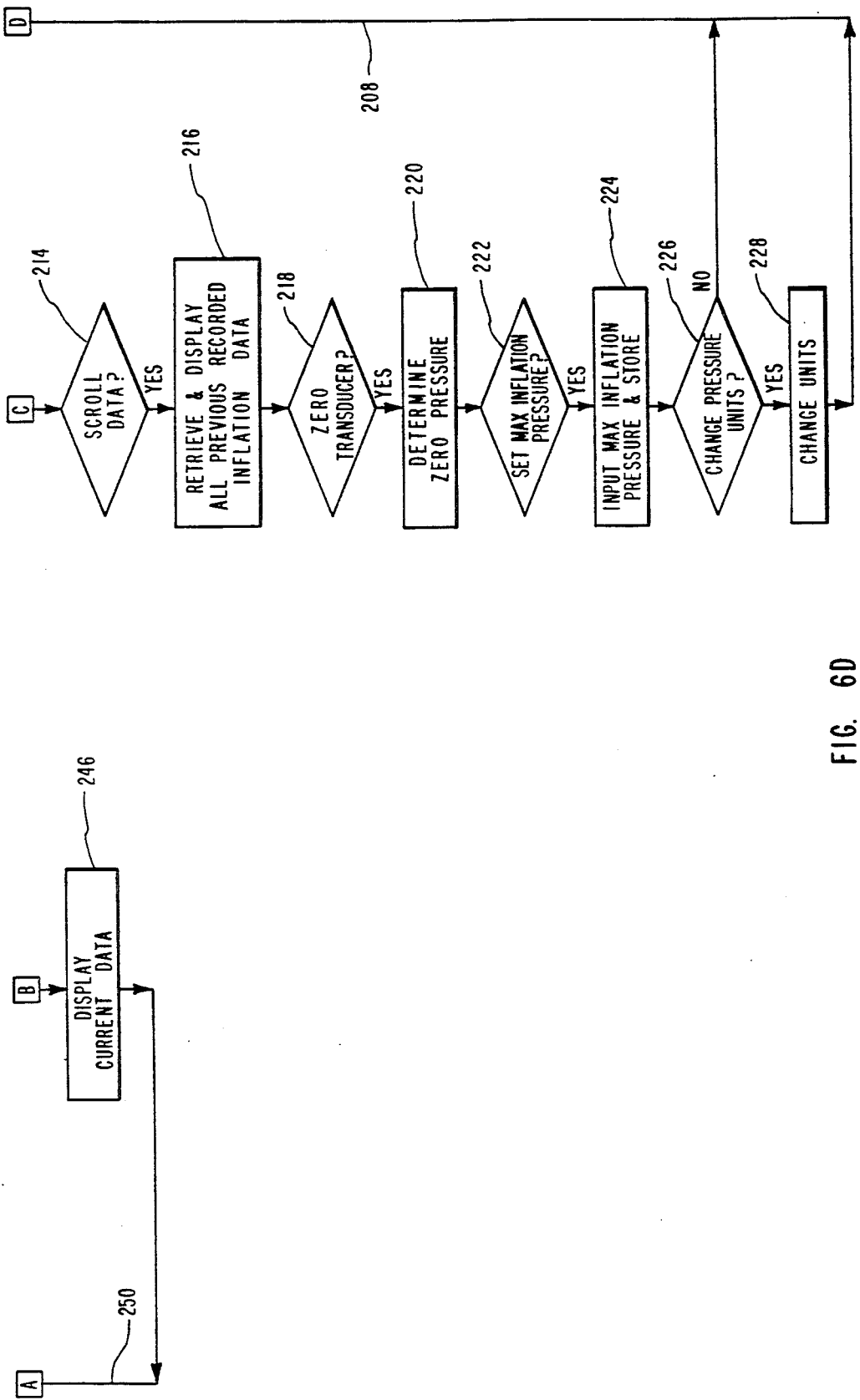
Figure 6D:
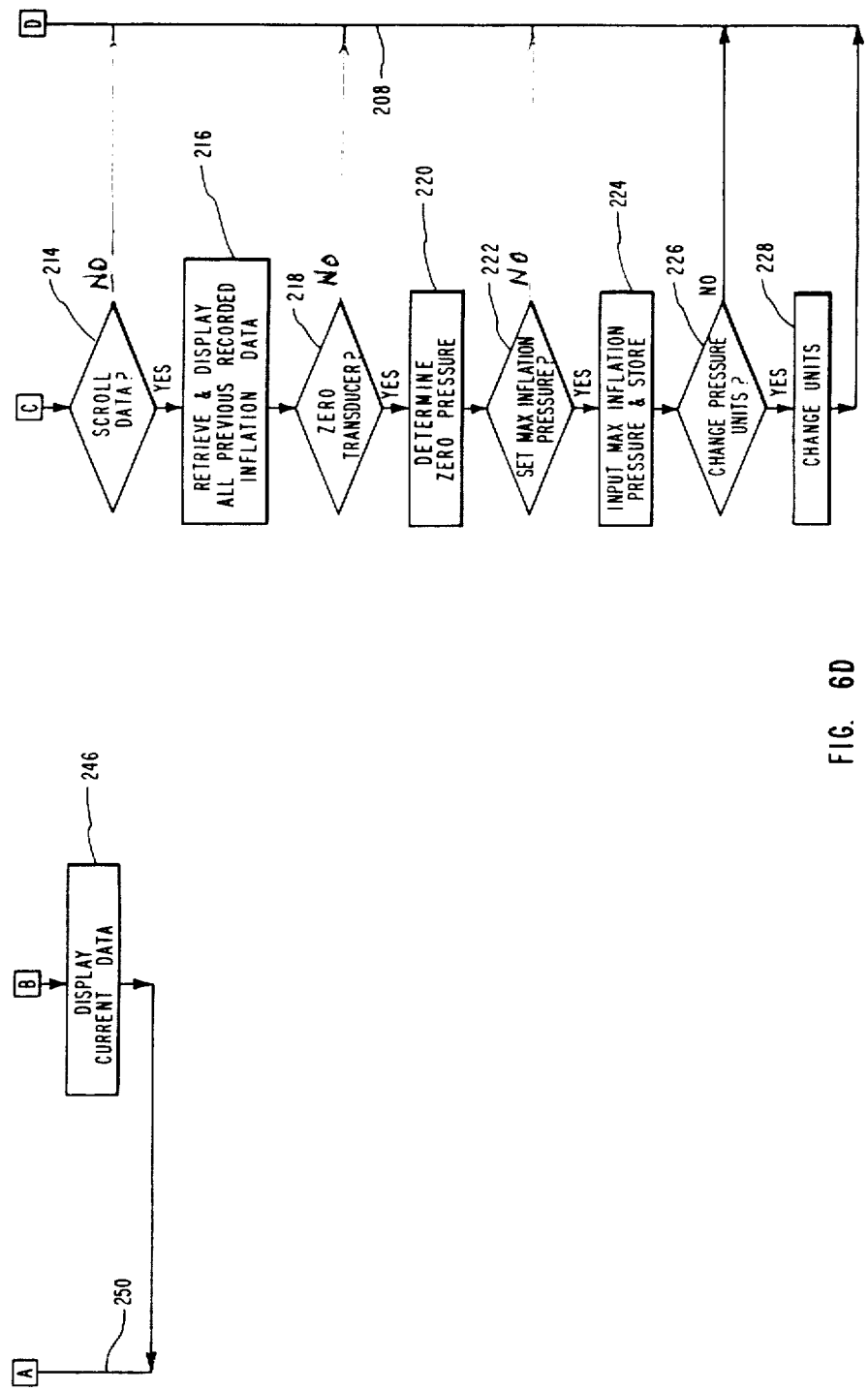

Once the transducer 42 has been connected to controller 20 the system moves to that portion of the program illustrated in FIGS. 6C and 6D where it then starts as schematically indicated at step 186 by moving to step 188 so that the electronic circuitry is permitted to stabilize. At this step the processor delays all operation of the electronic circuitry for a selected period of time to permit the circuit components to reach a steady state so that transient conditions will not introduce any errors into the data. The system then moves to step 190 where it determines the zero pressure of the transducer 42. At this step the processor means 90 determines the reading at transducer 42 with no pressure being applied. This zero pressure reading is then stored and is subsequently subtracted or offset against all other pressure readings to assure accuracy of the data.

At step 192 the system again undergoes a check to determine whether the transducer 42 is still connected to the controller 20. This is a safety precaution to make sure that at all times during the inflation procedure the transducer 42 is electrically connected to the controller 20 so that the data is being accurately input, displayed and recorded. If the transducer is not connected the system first updates the data memory 96 (step 193) so as to mark the time of disconnection and then a message is output as indicated at step 194 which notifies the system user that the transducer is disconnected and instructing the system user to press the menu switch 74. If the transducer 42 is still connected the system then moves to step 198 and begins to monitor the electrical signal from the transducer, which signal has been digitized and input to the digital processor as previously described in connection with FIGS. 4 and 5.

The signal from transducer 42 is monitored based on a sample rate that is a matter of design choice based upon the particular circuit design, which for the illustrated embodiment, is ten times per second. If the pressure which is sensed at transducer 42 is less than one-half atmosphere, the system moves to that portion of the program which commences with step 200. At that step the system first determines whether it is in the first pass through the loop started by step 200 and if so moves to step 202 where the memory is updated. The effect of updating the memory at step 202 is that the time with respect to termination of the last inflation is recorded and stored in the data memory 96. Once that step has been completed, the system then moves to step 204. In the alternative, if at step 200 the system determines that it is not the first pass through this loop of the program, the system moves directly to step 204 and displays the current data with respect to the inflation number, time, and pressure. The system then moves to step 206 where the processor checks the menu switch 74.

If the menu switch is activated in this condition the system moves to the next step 210 where the last inflation data can be marked as an initial test or not, as desired by the system user. If the initial inflation is merely a test it is marked at step 212 prior to returning to step 192, otherwise the system moves to step 214 to determine whether any previously recorded inflation data is to be scrolled. If the data is scrolled the system moves to step 216 and retrieves and displays in sequence all previously recorded inflation data for each prior inflation event, otherwise the system jumps to step 218.

Similarly, the system can also proceed through steps 218, 222, and 226 which will permit the transducer to again be zeroed (step 220), or to set a new maximum positive inflation pressure (step 224) or to change the pressure units (step 228) by entering any of these selections using the select switch 76.

Once the inflation pressure applied to the balloon catheter begins to exceed one-half atmosphere by insertion of the syringe plunger, the system moves from step 198 to the program step 230. At that step the system determines whether this is the first time through the part of the program loop which beings with step 230 and if so updates the memory at step 232. The effect of updating the memory at step 232 is that the processor causes the duration of the previous inflation to be recorded. After update memory step 232 has been performed, or in each subsequent pass through step 230, the system then moves to step 234 where the system checks to determine whether the inflation pressure has reached any selected maximum positive inflation pressure input for this inflation event. If the selected maximum inflation pressure is reached the system moves to step 238 and causes the pressure display readout 72 on control panel 64 to begin flashing so as to signal the system user that the selected maximum inflation pressure has been reached. If the selected maximum inflation pressure has not been reached or if none was selected, the system then jumps as illustrated at line 236 to step 240.

At step 240 the system checks to determine whether any selected duration has yet been clocked with respect to a selected duration for application of positive pressure and if so then moves to step 244 so as to cause the time display readout 70 to begin flashing, thereby signalling the system user that the selected duration has been achieved. If no duration is input or if the selected duration has not been reached the system moves to step 246 as indicated at line 242 which causes the system to display the current data with respect to the inflation pressure being applied and the length of time that positive inflation pressure has been applied. The system then returns to the beginning of the loop at step 192.

It will be appreciated that the digital processor U1 of FIG. 5A, which is an 8032 microprocessor as identified in Table I, could be programmed so as to implement the abovedescribed method using any one of a variety of different programming languages and programming techniques. Attached hereto as Appendix A is one such program which was prepared for use with the 8032 microprocessor and the circuit configuration as illustrated in FIGS. 5A and 5B. The attached program comprises a listing of source code and assembly language for the 8032 microprocessor.

The invention may be embodied in other specific forms without departing from its spirit or essential characteristics. Accordingly, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

TABLE I

| Schematic Reference | Part |
| --- | --- |
| X1 | 11.059 MHZ |
| C3 | 10Mfd |
| R1 | 8.2K |
| U1 | 8032 |
| U2 | 74HC573 |
| C5, C7, C14 | .01Mfd |
| C1, C2 | 33pf |
| P1 | CONNECTOR DB25F AMP 745389-1 |
| U4 | DS1243 |
| U5, U6, U7 | DL3416 SIEMENS |
| U8 | ADC0834 TI |
| U9 | MAX233 |
| D1 | IN5291 |
| R4 | 30K |
| U3 | 27256 |
| U11 | UA7805UC FAIRCHILD |
| C4 | 4700 Mfd |
| PCB 1 | Printed circuit board |
| JP3 | Female RJ-11 (6 pos- 4 wire) |
| JP1 | HEADER 4 |
| J1 | AC line cord |
| R17 | MMSI TRANSDUCER |
| R3 | 33K |
| U10 | LM324 |
| R5 | 10 K DIP |
| R7, R9, R10, R11 | 10K DIP |
| K6, R8 | 10K-15T VRN 752-208-103 |
| R12, R13 | 100K |
| R2 | 10K |
| C6, C8, C9, C10, C11, C12, C13 | .01 Mfd |
| C15, C16 | .2 Mfd |
| T1 | Toltek Custom transformer |
| D2 | GI 2KBP04 |
| F1 | .25 AMP |
| SW1 | Micro Switch & Cover |

What is claimed is:

1. A system for monitoring inflation of a balloon-type member and for automatically recording inflation data, comprising:
    a syringe connected to said member through tubing, said syringe comprising a barrel and a plunger selectively operable to inflate said member by applying fluid pressure to said member through said tubing by sliding the plunger within the barrel;
    transducer means for sensing said applied fluid pressure and for outputting an electrical signal proportional to said sensed fluid pressure, said transducer means being placed in fluid communication with said syringe and the tubing connected thereto;
    means for converting said signal output from said transducer means into a series of corresponding digital signals;

digital processor means for processing said digtial signals so as to electronically monitor, display and record inflation pressure applied to said member and the duration of inflation by performing the steps of:
    deriving data from said digital signals which represents a numerical value of the magnitude of said applied pressure;
    deriving data from said digital signals which represent a numerical value of the duration of said inflation pressure;
    electronically storing all said derived data for later retrieval and output; and
    automatically displaying said numerical values in a visually perceptible manner to a system user once said applied pressure exceeds a selected threshold level;
data memory means for storing the digital data derived by said digital processor means for later retrieval and output;
program memory means for storing machine-readable instructions utilized by said digital processor means to carry out said programmed steps; and
display means, electrically connected to said digital processor means, for outputting a visual display of the magnitude of said applied fluid pressure and the corresponding length of time said pressure is applied to said member.

2. A system as defined in claim 1 wherein said transducer means comprises a piezoresistive semiconductor transducer.

3. A system as defined in claim 2 wherein said transducer is mounted to said syringe so as to form an integral part thereof.

4. A system as defined in claim 3 further comprising an electrical cable attached at one end thereof to said transducer and comprising at the other end thereof a connector for attachment to said digital processor means.

5. A system as defined in claim 4 wherein said cable comprises a first length permanently attached to said transducer mounted on said syringe, and a second length of cable detachably connected to the first length, such that after said cable is connected to said digital processor means, said syringe and first length of cable may be disconnected from said second length of cable at a point along said cable that is intermediate said syringe and said digital processor means.

6. A system as defined in claim 1 wherein said display means is included within a controller.

7. A system as defined in claim 6 wherein said converting means, said digital processor means, said data memory means, and said program memory means are all included within said controller.

8. A system as claimed in claim 7 wherein said controller comprises a control panel and wherein said display means comprises a digital readout on said panel.

9. A system as defined in claim 8 wherein said display means further comprises means for outputting said digital data to a printer.

10. A system as defined in claim 9 wherein said control panel comprises:
    first switch means for selecting a menu display for presentation at said digital readout at least one of the following optionally selectable functions to be performed by said digital processor means:
    a. retrieving and reviewing all previously stored digital data;
    b. clearing all digital data previously stored in said data memory means;
    c. setting a maximum positive inflation pressure value;
    d. setting a maximum inflation time value;
    e. initializing date and time;
    f. selecting units of inflation pressure;
    g. printing data stored in said data memory means; and second switch means for entering to said digital processor means data identifying choices selected with respect to any of said functions.

11. A system for generating a series of discrete balloon catheter inflations and for automatically displaying and recording inflation data corresponding to each said discrete inflation, comprising:
    a control syringe connected to a balloon of said balloon catheter through tubing, said syringe comprising a barrel and a plunger selectively operable to first apply and then remove positive fluid pressures to said balloon through said tubing by sliding the plunger within the barrel;
    a piezoresistive semiconductor transducer connected in fluid communication with said fluid pressures applied to said balloon such that said transducer senses fluid pressures applied to said balloon and generates an electrical signal proportional to the sensed fluid pressure; and
    a controller electrically connected to said transducer, said controller comprising:
    means for amplifying said signal output by said transducer;
    means for converting said amplified signal from an analog to a digital form;
    digital processor means for processing said digital form of said signal so as to electronically monitor, display and record inflation pressure applied to said balloon and the duration of inflation by performing the steps of:
        deriving data from said digital signals which represents a numerical value of the magnitude of said applied pressure;
        deriving data from said digital signals which represent a numerical value of the duration of said inflation pressure;
        electronically storing all said derived data for later retrieval and output; and
        automatically displaying said numerical values in a visually perceptible manner to a system user once said applied pressure exceeds a selected threshold level;
    data memory means for storing the digital data derived by said digital processor means for later retrieval and output; and
    program memory means for storing machine-readable instructions utilized by said digital processor means to derive, store, retrieve and display said digital data and to optionally display a series of functions for selection at said display means; and
    display means for visually identifying a numerical value for each discrete inflation together with corresponding numerical values of said inflation pressures and duration thereof.

12. A system as defined in claim 11 wherein said transducer is mounted on said barrel so as to form an integral part thereof.

13. A system as defined in claim 11 wherein said display means comprises a digital readout and means for outputting said digital data to a printer.

14. A system as defined in claim 13 wherein said controller further comprises:
first switch means for selecting a menu display for presentation at said digital readout at least one of the following optionally selectable functions to be performed by said digital processor means:
a. retrieving and reviewing all previously stored digital data;
b. clearing all digital data previously stored in said data memory means;
c. setting a maximum positive inflation pressure value;
d. setting a maximum inflation time value;
e. initializing date and time;
f. selecting units of inflation pressure;
g. printing data stored in said data memory means; and second switch means for entering to said digital processor means data identifying choices selected with respect to any of said functions.

15. In a system for generating a series of discrete balloon catheter inflations and for automatically recording inflation data derived from an electrical signal corresponding to each said discrete inflation, an improved control syringe comprising:
a barrel connected through tubing to a balloon of said balloon catheter;
a plunger slidably mounted within said barrel and operable to selectively apply and then release fluid pressure on said balloon by movement of the plunger within said barrel;
a piezoresistive semiconductor transducer mounted on said syringe barrel and in fluid communication with the interior of said syringe barrel through a hole formed in a side of said syringe barrel such that changes in fluid pressure applied to said balloon by sliding said plunger are sensed by said transducer, which in turn generates an electrical signal proportional to the sensed positive fluid pressure; and
means for preventing said syringe plunger from occluding said hole.

16. In a system comprising an inflatable balloon member connected through tubing to a syringe barrel and wherein a plunger slidably mounted within said barrel is moveable to selectively apply and then release fluid pressures exerted on said balloon member so as to selectively inflate said balloon member one or more times, a method of monitoring, displaying and automatically recording inflation data comprising the steps of:
selectively increasing fluid pressure applied to the balloon member by pushing said plunger into said syringe barrel;
sensing the fluid pressure applied by said syringe and outputting an electrical signal proportional to the sensed fluid pressure;
automatically electronically digitally processing the output electrical signal once a selected threshold level of the applied fluid pressure is reached so as to automatically derive and automatically record therefrom electronic digital data representing the magnitude of the applied fluid pressures and the length of time said fluid pressures are applied to the balloon member;
electronically outputting a visual display of the magnitude and the corresponding length of time that said fluid pressures are applied to the balloon member; and
releasing the fluid pressure applied to the balloon member by pulling said plunger toward the rear of the syringe barrel.

17. A method as defined in claim 16 further comprising the step of repeating each of said steps in connection with a second inflation of the balloon member.

18. A method as defined in claim 16 further comprising the steps of:
electronically selecting and storing a maximum magnitude of positive fluid pressure to be applied to said balloon member; and
electronically outputting an indication to a system user that signals when said maximum fluid pressure is applied to said balloon member.

19. A method as defined in claim 16 further comprising the steps of:
electronically selecting and storing a maximum duration for which said fluid pressures are to be applied to said balloon member; and
electronically outputting an indication to a system user that signals when said maximum duration has been reached.

20. In a system comprising a balloon catheter connected through tubing to a syringe barrel and wherein by movement of a plunger through the barrel fluid pressure applied to the balloon catheter may be selectively increased or decreased, a method of electronically monitoring, displaying and recording the applied fluid pressure each time the balloon catheter is inflated, the method comprising the steps of:
inflating a balloon of the balloon catheter a first time by pushing the plunger into the syringe barrel so as to apply a positive inflation pressure to the balloon;
sensing any applied fluid pressure using a piezoresistive semiconductor transducer placed in fluid communication with the applied pressure, and generating at said transducer an electrical signal proportional in magnitude and duration to said applied pressure;
converting said electrical signal to a series of corresponding digital signals and inputting said digital signals to a digital processor;
processing the digital signals using said digital processor to carry out a programmed method comprising the steps of:
deriving data from said digital signals which represents a numerical value of the magnitude of said applied pressure;
deriving data from said digital signals once the applied pressure reaches a selected threshold level, said data representing a numerical value of the duration of said positive inflation pressure;
electrically storing all said derived data for later retrieval and output;
automatically displaying said numerical values in a visually perceptible manner to a system user once said applied pressure exceeds a selected threshold level;
deflating the balloon by withdrawing the syringe plunger so as to remove the positive fluid pressure applied to the balloon; and
repeating each of the above-recited steps for a second inflation of the balloon.

21. A method as defined in claim 20 wherein said digital processor is housed within a controller which comprises a control panel having a digital readout, and wherein prior to said inflating step said digital processor performs the step of presenting a visual display at said digital readout of at least one of the following optionally selectable functions:
- a. retrieving and reviewing all previously stored digital data;
- b. clearing all digital data previously stored in said data memory means;
- c. setting a maximum positive inflation pressure value;
- d. setting a maximum inflation time value;
- e. initializing data and time;
- f. selecting units of inflation pressure;
- g. printing data stored in said data memory means.

22. A method as defined in claim 20 wherein prior to said inflating step said digital processor performs the steps of:
   electronically sensing whether said transducer is electrically connected to said digital processor; and
   when sensing that said transducer is not so connected, said digital processor outputting to a system user a signal to that effect.

23. A method as defined in claim 20 wherein prior to said inflating step said digital processor performs the steps of:
   presenting an optionally selectable input for determining a maximum positive inflation pressure; and
   electronically storing digital data corresponding to said maximum positive inflation pressure in response to a user-determined input.

24. A method as defined in claim 23 wherein said method carried out by said digital processor further comprises the step of presenting to a system user an indication of when said selected maximum positive inflation pressure is applied to said balloon.

25. A method as defined in claims 20 or 23 wherein prior to said inflating step said digital processor performs the steps of:
   presenting an optionally selectable input for a maximum duration during which positive inflation pressure is to be applied to said balloon; and
   electronically storing digital data corresponding to said selected maximum duration in response to a user-determined input.

26. A method as defined in claim 25 wherein said method carried out by said digital processor further comprises the step of presenting to a system user an indication of when said selected duration is reached.

* * * * *

UNITED STATES PATENT AND TRADEMARK OFFICE
CERTIFICATE OF CORRECTION

PATENT NO. : 5,135,488  
DATED : August 4, 1992  
INVENTOR(S) : Jerrold L. Foote, et al Page 1 of 2

It is certified that error appears in the above-indentified patent and that said Letters Patent is hereby corrected as shown below:

The drawing sheet consisting of Fig.6b should be deleted and the attached sheet containing Fig. 6D should be inserted.

Column 1, line 9, "twenty seven" should be --twenty-seven--.

Column 1, line 52, "build up" shuld be --build-up--.

Column 2, line 4, after "heart" insert --.--.

Column 2, line 33, after "sheath" insert --.--.

Column 7, line 14, "counter clockwise" should be --counterclockwise--.

Column 14, line 15, "are" should be --is--.

Column 15, line 66, "abovedescribed" should be --above-described--.

Signed and Sealed this

Twenty-sixth Day of October, 1993

Attest:

*Attesting Officer*

BRUCE LEHMAN

*Commissioner of Patents and Trademarks*